United States Patent [19]

Champion et al.

[11] Patent Number: 5,854,395
[45] Date of Patent: Dec. 29, 1998

[54] **CLONED *BORRELIA BURGDORFERI* VIRULENCE PROTEIN**

[75] Inventors: Cheryl I. Champion, Culver City; Michael A. Lovett, Los Angeles; David A. Haake, Culver City; James N. Miller, Northridge; David R. Blanco, Beverly Hills, all of Calif.

[73] Assignee: The Regents of the University of California, Oakland, Calif.

[21] Appl. No.: 719,124

[22] Filed: Sep. 24, 1996

Related U.S. Application Data

[62] Division of Ser. No. 261,825, Jun. 17, 1994, Pat. No. 5,558,933.

[51] Int. Cl.$^6$ .................................................. C07K 14/195
[52] U.S. Cl. .......................... 530/350; 530/825; 930/10; 930/200
[58] Field of Search .................... 530/350, 825; 930/10, 200

[56] References Cited

U.S. PATENT DOCUMENTS

| | | | |
|---|---|---|---|
| 5,178,859 | 1/1993 | Simon et al. | 424/85.8 |
| 5,217,872 | 6/1993 | Dorward et al. | 435/7.32 |
| 5,246,844 | 9/1993 | Norris et al. | 432/172.3 |
| 5,279,938 | 1/1994 | Rosa | 435/6 |
| 5,283,175 | 2/1994 | Weaver et al. | 435/6 |
| 5,324,630 | 6/1994 | LeFebvre et al. | 435/6 |
| 5,403,718 | 4/1995 | Dorward et al. | 435/7.32 |
| 5,434,077 | 7/1995 | Simon et al. | 435/243 |

OTHER PUBLICATIONS

Maconi et al., "Analysis of the distribution and Molecular Heterogeneity of the OspD Gene amoung the Lyme Disease Spirochetes: Evidence for Lateral Gene Exchange", *Journal of Bacteriology*, vol. 176, No. 15, pp. 4572–4582, Aug. 1994.

Lam et al., "Outer Surface Proteins E and F of *Borrelia Burgdorferi*, the Agent of Lyme Diesease", *Infection and Immunity*, vol. 67, pp. 290–298, Jan. 1994.

Aron et al., "Cloning and DNA sequence analysis of bmpC, a gene encoding a potential membraine Lipoprotein of *Borrelia burgdorfei*", *FEMS Microbiology Letters*, vol. 123, pp. 75–82, 1994.

*Primary Examiner*—Stephen Walsh
*Assistant Examiner*—Christine Saoud
*Attorney, Agent, or Firm*—Fish & Richardson, P.C.

[57] ABSTRACT

The present invention provides EppA polypeptide, a *Borrelia burgdorferi* virulence protein. This 17-kD outer membrane protein has been designated EppA for exported plasmid protein A.

1 Claim, 8 Drawing Sheets

```
  1  TCATTATTATTGTTAATTATTAAGTTTAGCAAATAAAAATTACCAAAATCTTAATCAACAATGCTTAATTGCGAACACCA     79
                                                                                        RBS
 80  AATAAGACTATTTGTTAGTCTTGTTCCTAATTCTTATTAGTATTGCTAATAAGAATGTATATAATAAAGCCTAGGAGAGG   158
                   -35               ←――――――→              -10
159  ATG AGA AAA ATA AGC CTA TTG TTA TTT TTA ATG TTA AGC ATT GAT TTA AGT GCT              218
     Met Arg Lys Ile Ser Leu Leu Leu Phe Leu Met Leu Ser Ile Asp Leu Ser Ala
219  TTT ATG AGT CAA GAT ATA AAA AAT TAT GAG AAA AAA GCT TTT TCT AAA GAA                  278
     Phe Met Ser Gln Asp Ile Lys Lys Asn Tyr Glu Lys Lys Ala Phe Ser Lys Glu
     ――――――CC01――――――
279  GAT TAT GAT TTA CTT AAC AAA AGA CTA GAT AAT TAT GAT TTT GAA AGT TAT GAT AAA          338
     Asp Tyr Asp Leu Leu Asn Lys Arg Leu Asp Asn Tyr Asp Phe Glu Ser Tyr Asp Lys
339  AGC TTT TTT TTT GCT AAA GCT CCA GAA ATT AGG GGA AGT TTA AGA AAA ATC GGA ATT AAA     398
     Ser Phe Phe Phe Ala Lys Ala Pro Glu Ile Arg Gly Ser Leu Arg Lys Ile Gly Ile Lys
```

FIG. 2A

```
399 GAA AAT AGC GTT TTA GAC GCA CTT GAT GTT GTG GGC TTT ATA AAA AGC AAA ATA ACA  458
    Glu Asn Ser Val Leu Asp Ala Leu Asp Val Val Gly Phe Ile Lys Ser Lys Ile Thr

459 ACT GAT TTC TTA TCT TTT ATT ATA ATG AAC ATA AAT AGT CTC ATA AAG GGC TAT CCA AAT  518
    Thr Asp Phe Leu Ser Phe Ile Ile Met Asn Ile Asn Ser Leu Ile Lys Gly Tyr Pro Asn

519 TCA ATT TTC GAT TAT TTA ATA CAA TTG GAT TCG GAT AAA ATT GAT TAT GCC GAA AAA TAT  578
    Ser Ile Phe Asp Tyr Leu Ile Gln Leu Asp Ser Asp Lys Ile Asp Tyr Ala Glu Lys Tyr

579 GGA GAA AAA GCT AGA GAG AAT TTT GAA GAA TCT TAT AAG AAA ATA ACG GCA GTT  638
    Gly Glu Lys Ala Arg Glu Asn Phe Glu Glu Ser Tyr Lys Lys Asp Lys Ile Thr Ala Val

639 AAA CAA ATA TTA AAA CAA ATT TTG GCA GAC TTG CCT AAA GAT TAATTTTAAAAAATAGCTTAAAAA  698
    Lys Gln Ile Leu Lys Gln Ile Leu Ala Asp Leu Pro Lys Asp *
                                                 --------CC03--------

699 GAAATAATTTATAACCTTATGAGGCGTATAGATAGCATTATATAAAGCGAGTAGAAAAGCCAAAATATCTTAATAATTG  758
```

FIG. 2B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 782 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: EppA ( i x ) FEATURE:
        ( A ) NAME/KEY: CDS
        ( B ) LOCATION: 159..680

( x i ) SEQUENCE DESCRIPTION: SEQ ID NO:1:

```
TCATTATTTG  TTAATTATTA  AGTTTAGCAA  ATAAAAATTA  CCAAAATCTT  AATCAACAAT       60

GCTTAATTTG  CGAACACCAA  ATAAGACTAT  TTGTTAGTCT  TGTTCTAATT  CTTATTAGTA      120

TTGCTAATAA  GAATGTATAT  AATAAAGCCT  AGGAGAGG  ATG  AGA  AAA  ATA  AGC        173
                                              Met  Arg  Lys  Ile  Ser
                                               1                       5
```

```
CTA  TTG  TTA  TTT  TTA  TTA  TTT  ATG  TTA  AGC  ATT  GAT  TTA  AGT  GCT  TTT     221
Leu  Leu  Leu  Phe  Leu  Leu  Phe  Met  Leu  Ser  Ile  Asp  Leu  Ser  Ala  Phe
               10                  15                            20

ATG  AGT  CAA  GAT  ATA  AAA  AAA  AAT  TAT  GAG  AAA  GCT  AAA  AAA  GCT  TTT     269
Met  Ser  Gln  Asp  Ile  Lys  Lys  Asn  Tyr  Glu  Lys  Ala  Lys  Lys  Ala  Phe
               25                       30                       35

TCT  AAA  GAA  GAT  TAT  GAT  TTA  CTT  AAC  AAA  AGA  CTA  GAT  AAT  TAT  GAT     317
Ser  Lys  Glu  Asp  Tyr  Asp  Leu  Leu  Asn  Lys  Arg  Leu  Asp  Asn  Tyr  Asp
          40                            45                       50

TTT  GAA  AGT  GAA  TAT  GAT  AAA  AGC  TTT  TTT  TTT  GCT  AAA  GCT  CCA  GAA     365
Phe  Glu  Ser  Glu  Tyr  Asp  Lys  Ser  Phe  Phe  Phe  Ala  Lys  Ala  Pro  Glu
          55                            60                       65

ATT  AGG  GGA  AGT  TTA  AGA  AAA  ATC  GGA  ATT  AAA  GAA  AAT  AGC  GTT  TTA     413
Ile  Arg  Gly  Ser  Leu  Arg  Lys  Ile  Gly  Ile  Lys  Glu  Asn  Ser  Val  Leu
70                       75                       80                            85

TTA  GAC  GCA  CTT  GAT  GTT  GTG  GGC  TTT  ATA  AAA  AGC  AAA  ATA  ACA  ACT     461
Leu  Asp  Ala  Leu  Asp  Val  Val  Gly  Phe  Ile  Lys  Ser  Lys  Ile  Thr  Thr
                    90                       95                       100

GAT  TTC  TTA  TCT  TTT  ATT  ATA  ATG  AAC  ATA  AAT  AGT  CTC  ATA  AAG  GGC     509
Asp  Phe  Leu  Ser  Phe  Ile  Ile  Met  Asn  Ile  Asn  Ser  Leu  Ile  Lys  Gly
               105                      110                      115

TAT  CCA  AAT  TCA  ATT  TTC  GAT  TAT  TTA  ATA  CAA  TTG  GAT  TCG  GAT  AAA     557
Tyr  Pro  Asn  Ser  Ile  Phe  Asp  Tyr  Leu  Ile  Gln  Leu  Asp  Ser  Asp  Lys
          120                            125                      130

ATT  GAT  TAT  GCC  GAA  AAA  TAT  GGA  GAA  AAA  GCT  AGA  GAG  AAT  TTT  GAA     605
Ile  Asp  Tyr  Ala  Glu  Lys  Tyr  Gly  Glu  Lys  Ala  Arg  Glu  Asn  Phe  Glu
     135                      140                      145

GAA  TCT  TAT  AAG  AAA  GAT  AAA  ATA  ACG  GCA  GTT  AAA  CAA  ATA  TTA  AAA     653
Glu  Ser  Tyr  Lys  Lys  Asp  Lys  Ile  Thr  Ala  Val  Lys  Gln  Ile  Leu  Lys
150                      155                      160                           165

CAA  ATT  TTG  GCA  GAC  TTG  CCT  AAA  GAT  TAATTTAAA  AATAGCTTAA                   700
Gln  Ile  Leu  Ala  Asp  Leu  Pro  Lys  Asp
                    170

AAAGAAATAA  TTTATAACCT  TATGAGGCGT  ATAGATAGCA  TTATATAAAG  CGAGTAGAAA               760

AGCCAAAATA  TCTTAATAAT  TG                                                           782
```

( 2 ) INFORMATION FOR SEQ ID NO:2:

( i ) SEQUENCE CHARACTERISTICS:
        ( A ) LENGTH: 174 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Lys  Ile  Ser  Leu  Leu  Leu  Phe  Leu  Leu  Phe  Met  Leu  Ser  Ile
1                   5                        10                       15

Asp  Leu  Ser  Ala  Phe  Met  Ser  Gln  Asp  Ile  Lys  Lys  Asn  Tyr  Glu  Lys
               20                       25                       30

Ala  Lys  Lys  Ala  Phe  Ser  Lys  Glu  Asp  Tyr  Asp  Leu  Leu  Asn  Lys  Arg
          35                       40                       45

Leu  Asp  Asn  Tyr  Asp  Phe  Glu  Ser  Glu  Tyr  Asp  Lys  Ser  Phe  Phe  Phe
     50                       55                       60

Ala  Lys  Ala  Pro  Glu  Ile  Arg  Gly  Ser  Leu  Arg  Lys  Ile  Gly  Ile  Lys
65                       70                       75                       80

Glu  Asn  Ser  Val  Leu  Leu  Asp  Ala  Leu  Asp  Val  Val  Gly  Phe  Ile  Lys
               85                       90                       95

Ser  Lys  Ile  Thr  Thr  Asp  Phe  Leu  Ser  Phe  Ile  Ile  Met  Asn  Ile  Asn
```

|     |     |     |     |     |     |     |     |     |     |     |     |     |     |
| --- | --- | --- | --- | --- | --- | --- | --- | --- | --- | --- | --- | --- | --- |
|     |     |     |     | 100 |     |     |     |     | 105 |     |     |     | 110 |
| Ser | Leu | Ile | Lys | Gly | Tyr | Pro | Asn | Ser | Ile | Phe | Asp | Tyr | Leu | Ile | Gln |
|     |     |     | 115 |     |     |     | 120 |     |     |     |     | 125 |     |
| Leu | Asp | Ser | Asp | Lys | Ile | Asp | Tyr | Ala | Glu | Lys | Tyr | Gly | Glu | Lys | Ala |
|     |     | 130 |     |     |     | 135 |     |     |     | 140 |     |     |
| Arg | Glu | Asn | Phe | Glu | Glu | Ser | Tyr | Lys | Lys | Asp | Lys | Ile | Thr | Ala | Val |
| 145 |     |     |     | 150 |     |     |     |     | 155 |     |     |     |     | 160 |
| Lys | Gln | Ile | Leu | Lys | Gln | Ile | Leu | Ala | Asp | Leu | Pro | Lys | Asp |
|     |     |     |     | 165 |     |     |     | 170 |

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: CC01

(ix) FEATURE:
        (A) NAME/KEY: CDS
        (B) LOCATION: 1..18

(xi) SEQUENCE DESCRIPTION: SEQ ID NO:3:

ATGAGAAAAA TAAGCCTA                                      18

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: CC02

(ix) FEATURE:
        (A) NAME/KEY: CDS
        (B) LOCATION: 1..30

(xi) SEQUENCE DESCRIPTION: SEQ ID NO:4:

CGCGGATCCT TTATGAGTCA AGATATAAAA                        30

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: CC03

(ix) FEATURE:
        (A) NAME/KEY: CDS
        (B) LOCATION: 1..31

(xi) SEQUENCE DESCRIPTION: SEQ ID NO:5:

CCGGAATTCT TAATCTTTAG GCAAGTCTGC C                    31

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: CC04

( i x ) FEATURE:
        ( A ) NAME/KEY: CDS
        ( B ) LOCATION: 1..27

( x i ) SEQUENCE DESCRIPTION: SEQ ID NO:6:

CGCGGATCCA TGAGAAAAAT AAGCCTA     27

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: OspA-1

( i x ) FEATURE:
        ( A ) NAME/KEY: CDS
        ( B ) LOCATION: 1..21

( x i ) SEQUENCE DESCRIPTION: SEQ ID NO:7:

ATGAAAAAAT ATTTATTGGG A     21

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: OspA-2

( i x ) FEATURE:
        ( A ) NAME/KEY: CDS
        ( B ) LOCATION: 1..22

( x i ) SEQUENCE DESCRIPTION: SEQ ID NO:8:

TTTTAAAGCG TTTTTAATTT CA     22

CLONED *BORRELIA BURGDORFERI* VIRULENCE PROTEIN

This is a divisional of application Ser. No. 08/261,825, filed Jun. 17, 1994, now U.S. Pat. No. 5,558,933.

This application was made with Government support under Grant No. Al-29733 from the National Institutes of Health. The Government has certain rights in the invention.

BACKGROUND OF THE INVENTION

1. Field of the Invention

This invention relates generally to an antigenic preparation and specifically to a *Borrelia burgdorferi* protein (EppA, for exported plasmid protein A) which is used to induce a protective immune response in animals. This protein can be used immunologically as a vaccine for Lyme disease caused by this organism. Alternatively, diagnosis of Lyme disease can be performed by detecting the presence of the protein, antibody to the protein, or polynucleotide which encodes the protein.

2. Description of Related Art

Lyme disease is an infection with world-wide distribution caused by the spirochete *Borrelia burgdorferi*, and is the most commonly reported arthropodborne disease in the United States. About 10,000 reported cases of Lyme disease occur every year in the United States, caused by deer-tick bites that transmit the *Borrelia burgdorferi* organism. If not identified early, by flu-like symptoms and the bull's-eye rash that usually appears at the site of infection, untreated Lyme disease can cause heart problems, arthritis, and neurological symptoms. A large group of patients suffer from lasting neurological symptoms, including vision loss, that can recur for years as a result of Lyme disease.

The genus Borrelia is unique among the pathogenic spirochetes in that it contains both linear and circular plasmids which account for approximately 150-kbp of the total genetic material (A. G. Barbour, *J. Clin. Microbiol.*, 26:475–478, 1988; Hinnebusch, et al., *J. Bacteriol.*, 174:5221–5227, 1992; Hinnebusch, et al., *J. Bacteriol*, 173:7233–7239, 1991; Hinnebusch, et al., *Mol. Microbiol.*, 4:811–820, 1990; Howe, et al., *Science*, 82:151–154, 1985; Hyde, et al.,*J. Clin. Microbiol.*, 20:151–154, 1984; Schwan, et al., *Infec. Immun.*, 56:1831–1836, 1988; Simpson, et al., *J. Clin. Microbiol.*, 28:1329–1337, 1990; Simpson, et al., *Microbiol. Path.*, 8:109–118, 1990). Only genes for the outer surface lipoproteins (Osps A, B, C, D, E, and F) have been mapped to these plasmids. The ospAB and ospEF operons have been mapped to linear plasmids of 49- and 45-kbp, respectively (Bergstron, et al., *Mol. Microbiol.*, 3:479–486, 1986; Lam, et al., *Infect. Immun.*, 62:290–298, 1994), while the gene encoding ospD resides on a 38-kbp linear plasmid (Norris, et al., *Infec. Immun.*, 60:4662–4672, 1992). The ospC locus has recently been localized to a 26-kbp circular plasmid and represents the first *B. burgdorferi* gene to be mapped to a circular plasmid (Fuchs, et al., *Mol. Microbiol.*, 6:503–509, 1992; U. K. Laemmli, *Nature*, 227:680–685, 1970). Since many pathogenic bacteria harbor plasmids which encode genes whose expression is required for virulence, it is likely that genes encoding potential virulence determinants are also present on plasmids of *B. burgdorferi.*

The study of *B. burgdorferi* plasmids, with respect to virulence, has been limited by the lack of spirochete genetic exchange systems. Recently, one approach to studying these plasmids was developed based on the concept underlying TnphoA transposition (Boquet, et al., *J. Bacteriol.*, 169:1663–1669, 1987; Hoffman, et al., *Proc. Natl. Acad. Sci. USA*, 82:5107–5111, 1985; Manoil, et al., *Science*, 233:1403–1408, 1986; Manoil, et al., *J. Bacteriol.*, 172:515–518, 1990). The system utilizes a phoA expression vector termed pMG, that contains an alkaline phosphatase (AP) gene lacking its signal sequence, together with the *E. coli* mutant strain KS330 (Strauch, et al., *Proc. Natl. Acad. Sci. USA*, 85:1575–1580, 1988), which possesses a leaky outer membrane, to identify genes encoding signal peptide export-dependent proteins which may function as virulence determinants. The utility of this system has been confirmed for both *Treponema pallidum* (Blanco, et al., *Mol. Microbiol.*, 5:2405–2415, 1991) and *Leptospira alstoni* in which signal peptide containing proteins from both organisms were shown to be exported in *E. coli.*

The pMG/KS330 system was utilized in identification of a *B. burgdorferi* B31 recombinant, termed Bb244, that was generated from a library of the 9.0-kbp circular plasmid (Giladi, et al., *J. Bacteriol.*, 175:4129–4136, 1993). It had previously been reported by Schwan, et al. (Schwan, et al., supra) and later by Simpson, et al. (Simpson, et al., supra), that in *B. burgdorferi* strain SH-2-82, the loss of two similar sized circular plasmids (8.4- and 8.8-kbp) following 20 in vitro passages was correlated with the loss of virulence. Bb244 was shown to have an open reading frame, a typical signal peptide containing a type I leader peptidase cleavage site, translational, and transcriptional sequences upstream of the ATG start codon (Giladi, et al., supra).

There is a need to identify outer membrane proteins of *Borrelia burgdorferi* that may be associated with virulence of this spirochete. Such a protein would allow specific diagnosis of Borrelia infection and also be an excellent vaccine candidate for the prevention of such Borrelia associated diseases as Lyme disease.

SUMMARY OF THE INVENTION

The present invention is based on the identification of the novel protein EppA which is a *Borrelia burgdorferi* exported protein associated with virulence of Borrelia. The invention describes a 17 kD outer membrane protein from *Borrelia burgdorferi* and the gene encoding the protein. This gene is encoded on a 9-kb plasmid within the organism and is present during the infectious, in vivo stages of virulent *Borrelia burgdorferi* growth. The deduced amino acid sequence for EppA (the EppA polypeptide) has a typical leader peptidase I cleavage site, implying export beyond the inner membrane. The 17-kD EppA polypeptide has been designated EppA for exported plasmid protein A. This polypeptide is useful for inducing an immune response to *B. burgdorferi* as well as providing a diagnostic target for Lyme disease.

BRIEF DESCRIPTION OF THE DRAWINGS

FIG. 2 shows the nucleotide and deduced amino acid sequences of eppA (SEQ ID NO:1 for the eppA polynucleotide sequence and SEQ ID NO:2 for the EppA polypeptide sequence. The putative ribosome-binding site (RBS) and –10 and –35 promoter regions are underlined. A region of dyad symmetry within the –35 promoter site is indicated by inverted arrows. The leader peptidase I cleavage site is noted by an arrow (↑). The location of the TAA stop codon is indicated by an asterisk. Sequence location for PCR primers CC01, CC02, and CC03 are indicated.

FIG. 6A shows the separation of cytoplasmic membrane from outer membrane (OM) based on $\beta$-NADH oxidase activity (■). FIGS. 6B and 6C are identical immunoblots containing 10% of each fraction (1–12, T=total lysate before gradient) incubated with 1:10,000 dilution of rabbit anti-OmpA and 1:1000 dilution of rabbit anti-EppA, respectively. FIG. 6D is a immunoblot of alkali and high salt treatment of the enriched OM fraction. The OM was treated with 0.1M $Na_2CO_3$ (pH 11.5) (lanes 2 and 3), 0.1N NaOH (pH 11.0) (lanes 4 and 5), and 1M NaCl (lanes 6 and 7), followed by centrifugation to separate soluble (S) from the membrane pelleted (P) material. The samples were separated on a SDS-12.5% polyacrylamide gel, transferred to Immobilon-P, and incubated with a 1:1000 dilution of rabbit anti-EppA. Molecular masses (in kilodaltons) of prestained protein markers are indicated.

DETAILED DESCRIPTION OF THE INVENTION

Figure 1:
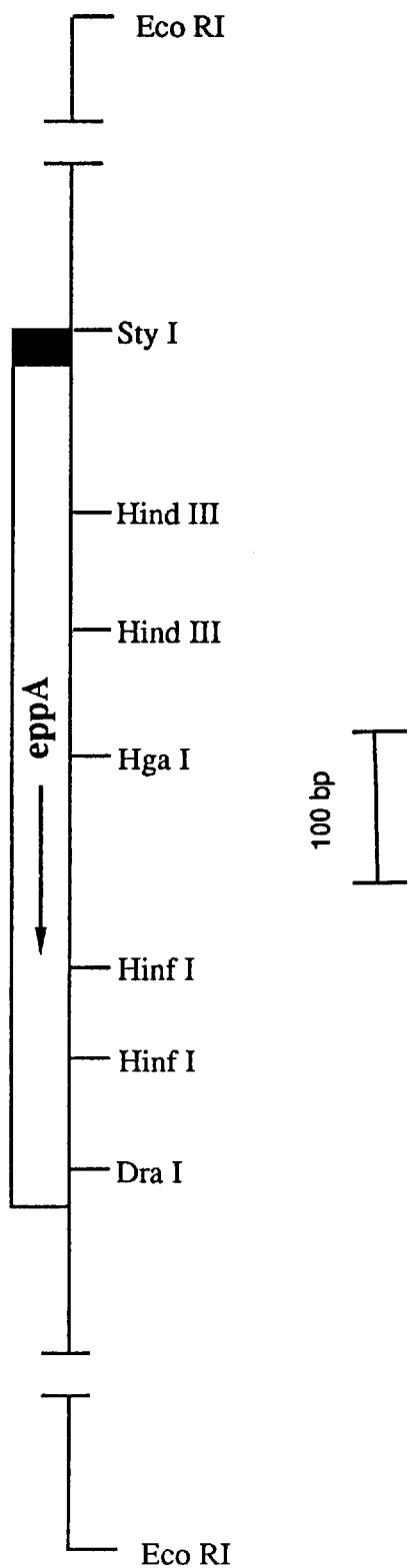
FIG. 1 shows a partial restriction map of the 3.3-kbp EcoRI fragment in pBb1. The shaded area in indicates the location of the EppA signal peptide. The open boxed area indicates the coding region for mature EppA. (bp, Base pairs).

The present invention provides an isolated immunogenic polypeptide which is an exported protein of a *Borrelia burgdorferi*. Also included is a polynucleotide sequence which encodes the polypeptide. The protein is encoded by a gene on a 9.0-kb circular plasmid of *B. burgdorferi*. This immunogenic polypeptide is useful in a pharmaceutical composition for inducing an immune response to virulent *B. burgdorferi*.

The invention includes a method of producing the polypeptide using recombinant DNA techniques. The gene for EppA was cloned into a plasmid vector which was then used to transform *E. coli*. When the eppA gene was expressed in *E. coli*, the polypeptide produced had a molecular weight of approximately 17-kD as determined by SDS-polyacrylamide gel electrophoresis. Reactivity to the 17-kD protein was demonstrated with antisera to recombinant EppA. This polypeptide is an excellent vaccine candidate as well as a marker antigen for diagnosis of Lyme borreliosis.

Sequence analysis showed that the eppA structural gene consists of 522 base pairs encoding a precursor protein of 174 amino acids, with typical N-terminus characteristics of a signal peptide, that is, an amino terminus beginning with methionine and basic charged residues, a hydrophobic core, and a leader peptidase I recognition site containing the amino acid sequence, Leu-Ser-Ala. Therefore, as would be expected for a protein to be exported beyond the inner membrane, the derived amino acid sequence begins with a signal peptide.

Minor modifications of EppA primary amino acid sequence may result in proteins which have substantially equivalent function compared to the EppA protein described herein. Such modifications may be deliberate, as by site-directed mutagenesis, or may be spontaneous. All proteins and fragments thereof produced by these modifications are included herein as long as EppA function exists. For example, the functional fragment would contain a T-cell or B-cell epitope for induction of an immune response in a subject.

Modifications of EppA primary amino acid sequence also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Isolation and purification of microbially expressed protein, on fragments thereof, provided by the invention, may be carried out by conventional means including preparative chromatography and immunological separations involving monoclonal or polyclonal antibodies.

The invention extends to any host modified according to the methods described, or modified by any other methods, commonly known to those of ordinary skill in the art, such as, for example, by transfer of genetic material using a lysogenic phage, and which result in a prokaryote expressing the gene for EppA protein. Prokaryotes transformed with the gene encoding the EppA protein are particularly useful for the production of polypeptides which can be used for the immunization of an animal.

The invention provides polynucleotides encoding the *B. burgdorferi* EppA protein. These polynucleotides include DNA and RNA sequences which encode the protein. It is understood that all polynucleotides encoding all or a portion of EppA are also included herein, so long as they exhibit a function of EppA, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., *Nucleic Acid Research*, 9:879, 1981).

Alternatively, an expression library can be screened indirectly for EppA peptides having at least one epitope using antibodies to EppA. Such antibodies can be either polyclonally or monoclonally derived and used to detect expression product indicative of the presence of eppA DNA. Generally, a lambda λgt11 library is constructed and screened immunologically according to the method of Huynh, et al. (in *DNA Cloning:A Practical Approach*, D. M. Glover, ed., 1:49, 1985).

The development of specific DNA sequences encoding EppA can also be obtained by: (1) isolation of a double-stranded DNA sequence from the genomic DNA, and (2) chemical manufacture of a DNA sequence to provide the necessary codons for the polypeptide of interest.

DNA sequences encoding EppA can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of the EppA protein of *B. burgdorferi*. Prokaryotic hosts may include Gram negative as well as Gram positive bacteria, such as *E. coli, S. typhimurium*, and *Bacillus subtilis*.

A recombinant DNA molecule coding for the EppA protein can be used to transform a host using any of the techniques commonly known to those of ordinary skill in the art. Especially preferred is the use of a plasmid containing the EppA coding sequence for purposes of prokaryotic transformation. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, the eppA sequences may be inserted into a recombinant expression vector. The term "recombinant expression vector" refers to a plasmid, virus or other vehicle known in the art that has been manipulated by insertion or incorporation of eppA genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported (Heinemann, et al., *Nature*, 340:205, 1989; Rose, et al., *Gene*, 60:237, 1987). Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of *B. burgdorferi* EppA in prokaryotic hosts.

Examples of promoters which can be used in the invention are: rec A, trp, lac, tac, and bacteriophage lambda $p_R$ or $p_L$. Examples of plasmids which can be used in the invention are listed in Maniatis, et al.,(*Molecular Cloning*, Cold Spring Harbor Laboratories, 1982).

Antibodies provided in the present invention are immunoreactive with EppA protein. Antibody which consists essentially of pooled monoclonal antibodies with different epitopic specificities, as well as distinct monoclonal antibody preparations are provided. Monoclonal antibodies are made from antigen containing fragments of the protein or intact protein by methods well known in the art (Kohler, et al., *Nature*, 256:495, 1975; *Current Protocols in Molecular Biology*, Ausubel, et al., ed., 1989). Hybridoma producing antibody which bind EppA can be readily identified, for example, by screening hybridoma with EppA bound to a solid phase. Such techniques from the preparation and screening of immunoclonal antibodies are routine to those of ordinary skill in the art.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the EppA polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In one embodiment, the invention provides a pharmaceutical composition useful for inducing an immune response to virulent Borrelia in an animal comprising an immunologically effective amount of EppA in a pharmaceutically acceptable carrier. The term "immunogenically effective amount," as used in describing the invention, is meant to denote that amount of Borrelia antigen which is necessary to induce in an animal the production of an immune response to Borrelia. The EppA protein of the invention is particularly useful in sensitizing the immune system of an animal such that, as one result, an immune response is produced which ameliorates the effect of Borrelia infection.

The EppA protein can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate.

Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water.

Besides the inert diluents, such compositions can also include adjuvants, wetting agents, and emulsifying and suspending agents.

It is also possible for the antigenic preparations containing the EppA protein of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus Brucella).

In another embodiment, a method of inducing an immune response to virulent Borrelia in an animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Borrelia is desirable include humans, dogs, cattle, horses and sheep.

Generally, the dosage of EppA protein administered to an animal will vary depending on such factors as age, condition, sex and extent of disease, if any, and other variables which can be adjusted by one of ordinary skill in the art.

The antigenic preparations of the invention can be administered as either single or multiple dosages and can vary from about 10 ug to about 1,000 ug for the Borrelia EppA antigen per dose, more preferably from about 50 ug to about 700 ug EppA antigen per dose, most preferably from about 50 ug to about 300 ug EppA antigen per dose.

When used for immunotherapy, the monoclonal antibodies of the invention that binds to EppA may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

In a further embodiment, the invention provides a method of detecting a Borrelia-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for EppA may be used to detect the presence of EppA polypeptide (using antibody) or polynucleotide (using nucleic acid probe) in biological fluids or tissues. Any specimen containing a detectable amount of EppA antigen or polynucleotide can be used. A preferred specimen of this invention is blood, urine, cerebrospinal fluid, or tissue of endothelial origin.

When the cell component is nucleic acid, it may be necessary to amplify the nucleic acid prior to binding with a Borrelia specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, EppA polypeptide can be used to detect antibodies to EppA polypeptide in a specimen. The EppA of the invention is particularly suited for use in immunoassays in which it can be utilized in liquid phase or bound to a solid phase carrier. In addition, EppA used in these assays can be detectably labeled in various ways.

Examples of immunoassays which can utilize the EppA of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to the EppA of the invention can be done utilizing immunoassays which run in either the forward, reverse, or simultaneous modes, including immunohistochemical assays on physiological samples. The concentration of EppA which is used will vary depending on the type of immunoassay and nature of the detectable label which is used. However, regardless of the type of immunoassay which is used, the concentration of EppA utilized can be readily determined by one of ordinary skill in the art using routine experimentation.

The EppA of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding EppA or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to EppA of the invention may be present in various biological fluids and tissues. Any sample containing a detectable amount of antibodies to EppA can be used. Normally, a sample is a liquid such as urine, saliva, cerebrospinal fluid, blood, serum and the like, or a solid or semi-solid such as tissue, feces and the like. Preferably, the sample is serum from the patient.

The monoclonal antibodies of the invention, directed toward EppA, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of Borrelia EppA antigen for which the monoclonal antibodies are specific.

The concentration of detectably labeled monoclonal antibody which is administered should be sufficient such that the binding to those cells, body fluid, or tissue having EppA is detectable compared to the background. Further, it is desirable that the detectably labeled monoclonal antibody be rapidly cleared from the circulatory system in order to give the best target-tobackground signal ratio.

As a rule, the dosage of detectably labeled monoclonal antibody for in vivo diagnosis will vary depending on such factors as age, sex, and extent of disease of the subject. The dosage of monoclonal antibody can vary from about 0.001 $mg/m^2$ to about 500 $mg/m^2$, preferably 0.1 $mg/m^2$ to about 200 $mg/m^2$, most preferably about 0.1 $mg/m^2$ to about 10 $mg/m^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}In$, $^{97}Ru$, $^{67}Ga$, $^{68}Ga$, $^{72}As$, $^{89}Zr$, and $^{201}Tl$.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}Gd$, $^{55}Mn$, $^{162}Dy$, $^{52}Cr$, and $^{56}Fe$.

The monoclonal antibodies of the invention can be used to monitor the course of amelioration of Borrelia associated disorder. Thus, by measuring the increase or decrease of Borrelia EppA polypeptide or antibodies to EppA polypeptide present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a EppA binding reagent, such as an antibody. A second container may further comprise EppA polypeptide. The constituents may be present in liquid or lyophilized form, as desired.

The following examples are intended to illustrate but not limit the invention. While they are typical of those that might be used, other procedures known to those skilled in the art may alternatively be used.

EXAMPLES

The present invention provides the nucleotide sequence of the eppA gene (exported plasmid protein A), the deduced amino acid sequence, and evidence which suggests that eppA is expressed only during the course of infection with *Borrelia burgdorferi*. In addition, studies show that expression of recombinant EppA in *E. coli* results in localization to the outer membrane. Approximately 85% of 63 patients with documented Lyme borreliosis have antibodies which bind purified rEppA as determined by ELISA. Therefore, eppA correlates with infectivity for humans.

Example 1

Materials and Methods

Bacterial strains, plasmids, and media

Bacterial strains and plasmids used in this study are described in Table 1. Virulent *B. burgdorferi* B31 (B31V) and avirulent B31 (B31A) (ATCC 35210) were grown in BSK II media as previously described (A. G. Barbour, et al., *Yale J. Biol. Med*., 57:521–525, 1984). Infectivity for B31V was confirmed with C3H mice as previously described (Schwan, et al., supra). *Escherichia coli* strains were grown at 37° C. on Luria-Bertani medium.

DNA purification and manipulations

Approximately $9\times10^{11}$ *B. burgdorferi* B31V (passage 2) grown in BSK II at 34° C. were harvested for DNA extraction as described previously (Barbour, et al., Science, 237:409–411, 1987). Following enrichment of the circular plasmids by cesium chloride density gradients, approximately 120 μmg of circular plasmid was separated electrophoretically on a 0.5% preparative agarose gel and the 9.0-kbp circular plasmid was gel purified by silica gel chromatography (Geneclean II; Bio101, La Jolla, Calif.). Recombinant plasmid DNA was obtained by the method of Birnboim and Doly (Birnboim, et al., *Nucl. Acid Res*., 7:1513–1523, 1979) and purified using Qiagen columns (Qiagen, Inc., Chatsworth, Calif.).

All restriction endonucleases and DNA-modifying enzymes were used in accordance with the specifications of the manufacturer (Bethesda Research Laboratories, Inc., Gaithersburg, Md., or Boehringer Mannheim Biochemicals, Indianapolis, Ind.).

Synthetic oligonucleotides

Oligonucleotides used for probes and PCR primers are shown in Table 2. Custom primers were also made for DNA sequencing of pBb1. Oligonucleotides were synthesized by an Applied Biosystems model 470B automated DNA synthesizer (Applied Biosystems, Foster City, Calif.) and purified by OPC chromatography (Applied Biosystems).

PCR

PCR was performed according to the manufacturer's instructions using AmpliTaq (GeneAmp, Perkin-Elmer Cetus, Norwalk, Conn.) and a Programmable Thermal Controller (PTC-100, M.J. Research, Inc., Watertown, Mass.). Reactions of 50 μl were performed in 10 mM Tris-HCl (pH 8.3), 50 mM KCl, 2.0 mM $MgCl_2$, 0.001% (wt/vol) gelatin, 0.5 μM of each primer, 200 μM of each dNTP, 1 ng template, and 1.25 units of AmpliTaq. After overlaying with 50 μl of mineral oil, the reactions were performed for 30 cycles beginning with an initial denaturation step of 2 minutes at 94° C. followed by 30 seconds at 94° C., 30 seconds at 45° C., 30 seconds at 72° C., and a final extension step of 72° C. for 10 minutes. The amplification products were analyzed by agarose gel electrophoresis and purified by Geneclean II (Bio101).

Southern blot analysis Southern blot analysis was performed as described previously by Maniatis, et al., (Maniatis, et al., *Cold Spring Harbor Laboratory Press*, 1982). Probe CC01 was labeled at its 5' end with [γ-$^{32}$P]ATP (5,000 Ci/mmol; Amersham Corp., Arlington Heights, Ill.) and T4 polynucleotide kinase followed by purification over a BioSpin 6 column (Bio-rad Laboratories, Hercules, Calif.). Membranes were hybridized overnight at 37° C. with 1×10$^6$ cpm/ml of hybridization buffer.

Cloning of the eppA gene

A library of the 9.0-kbp circular plasmid was generated in the λ Zap II vector system (Stratagene, San Diego, Calif.). Following digestion with both EcoRV-HincII, the DNA fragments were EcoRI adapted (Boehringer Mannheim Biochemicals) and ligated into the phage vector. The library was packaged, plated, and amplified according to the manufacturer's recommendations. Approximately 1,000 plaques were plated, transferred to filters in duplicate, and processed as previously described (Maniatis, et al., supra). Probe CC01 was radiolabled as described above and used for plaque hybridizations. Positive recombinant pBluescript SK(−) clones were recovered by in vivo excision according to the manufacturer's instructions.

DNA sequencina and computer analysis

DNA was sequenced using the dideoxynucleotide chain termination method described by Sanger, (Pages, et al., *Eur. J. Biochem.*, 143:499–505, 1984). Standard M13 primers and custom oligonucleotide primers synthesized at UCLA, Dept. of Microbiology & Immunology, were used to sequence double-stranded templates. Sequencing reactions were performed for both strands using the Deaza T7 Sequencing kit protocol as described by Pharmacia Biotech, Inc., and [α-$^{35}$S]dATP (specific activity, 1,000 Ci/mmol). DNA and deduced amino acid sequences were analyzed using DNA Strider v. 1.0 (C. Marck, *Nucl. Acids Res.*, 16:1829–1836, 1988). Protein homology searches were performed with the Profilesearch and FASTA programs found in the University of Wisconsin Genetics Computer Group (GCG), Inc., package, ver. 7.0 (Devereux, et al., *Nuc. Acids Res.*, 12:387–395, 1984).

Northern blot analysis

Total cellular RNA was isolated from B31V (passage 2) and B31A by the hot-phenol method as previously described (von Gabian, et al., *Proc. Natl. Acad. Sci. USA*, 80:653–657, 1983). Approximately 15 μg of RNA from each sample was electrophoresed in duplicate through a 1.5% agarose-formaldehyde gel and transferred to nitrocellulose as previously described (Maniatis, et al., supra). The filters were probed separately with PCR-generated DNA fragments of either ospA or eppA genes radiolabled with [α-$^{32}$P]dATP using the Random Primers DNA Labeling System (BRL). Hybridizations were conducted as previously described (Maniatis, et al., supra).

Expression of His$_6$-EppA fusion protein

A 477-bp BamHI-EcoRI fragment containing eppA minus the nucleotide sequence of the signal peptide was generated by PCR utilizing primers CC02 and CC03 (Table 2). The purified PCR product was ligated into the pRSET expression vector (Invitrogen Corp., San Diego, Calif.) previously digested with BamHI-EcoRI. The resulting construct, pRSET-eppA, was transformed into *E. coli* JM109(DE3), a λ lysogen which contains a chromosomal copy of the T7 RNA polymerase gene under the control of the lacUV5 promoter. Expression of the His$_6$-EppA fusion protein was achieved by induction for 45 minutes with 1 mM isopropyl-β-D-thiogalactopyranoside (IPTG; Sigma Chemical Co., St. Louis, Mo.) followed by the addition of 200 ug/ml of rifampicin and then incubation for an additional 4 hours at 37° C. After incubation, the cells were pelleted and resuspended in 50 mM Na$_2$HPO$_4$ (pH 8.0), 300 mM NaCl, and lysed by multiple rounds of freeze-thaw and sonication. The lysed cells were centrifuged at 10,000×g for 30 minutes, and the resulting supernatant containing the His$_6$-EppA fusion protein was purified over a Ni-NTA resin column (Qiagen, Chatsworth, Calif.). Following purification, the fusion protein was cleaved with enterokinase thereby releasing the fusion peptide from EppA. Recombinant EppA (rEppA) was further purified by gel filtration using Sephacryl S-100 HR (Pharmacia Biotech Inc., Piscataway, N.J.).

Antisera

Rabbit anti-EppA antiserum was generated in New Zealand White male rabbits receiving approximately 150 ug of purified rEppA in 1 ml of PBS (phosphate buffered saline) mixed with 1 ml of Freund's complete adjuvant injected at four subcutaneous sites. Animals were boosted twice by the same route at 4-week intervals with approximately 75 ug of antigen in 1 ml of PBS mixed with 1 ml of Freund's incomplete adjuvant. Human Lyme borreliosis sera used in this study were collected from clinically diagnosed patients and kindly provided by Dr. Andrew Pachner (Georgetown Univ., Washington, D.C.). Normal human sera was obtained from the UCLA Clinical Laboratories. Sera from Lyme borreliosis rabbits immune to challenge were generated after 6 months from animals infected intradermally with 6×10$^7$ B31V.

Generation F(ab')2 fragments

Rabbit anti-EppA IgG and rabbit IgG were prepared using HiTrap Protein A affinity columns according to the manufacturer's instructions (Pharmacia Biotech, Inc.). F(ab')2 fragments were prepared by digestion of purified IgG with immobilized pepsin (Pierce Chemical Co., Rockville, Ill.) and undigested IgG was removed by the HiTrap Protein A affinity column. Purification of F(ab')2 fragments was determined by SDS-PAGE analysis and by ELISA.

SDS-PAGE and immunoblotting

SDS-polyacrylamide slab gels were run by using the discontinuous buffer system of Laemmli (U. D. Laemmli, *Nature*, 227:680–685, 1970). Samples were boiled for 10 minutes in final sample buffer (FSB) composed of 62.5 mM Tris-HCl (pH 6.8), 10% glycerol, and 2% SDS. After electrophoresis, separated proteins were transferred to Immobilon-P membranes (Millipore Corp., Bedford, Mass.) for immunoblotting or stained with Coomassie brilliant blue. For immunoblotting, membranes were incubated for 1 hour with serum diluted in PBS (phosphate-buffered saline) containing 5% nonfat dry milk (Carnation Co., Los Angeles, Calif.) and 0.1% Tween-20 (Sigma Chemical Co., St. Louis, Mo.) (MT-PBS). Following incubation, membranes were probed with anti-rabbit Ig or anti-human Ig conjugated to horseradish peroxidase (HRP) (Amersham) diluted 1:5000 in MT-PBS. Antigen-antibody binding was detected by using the Enhanced Chemiluminescence (ECL) System (Amersham) and exposed to X-OMAT AR film (Eastman Kodak Co., Rochester, N.Y.).

Antigen-capture ELISA

Flat-bottom 96-well Immunoassay plates (Immunlon 4, Dynatech Laboratories, Chantilly, Va.) were coated overnight at room temperature with either 100 ul of purified anti-EppA IgG F(ab')2 fragments diluted to a concentration of 10 ug/ml in PBS (0.14M NaCl, 2.7 mM KCl, 4.3 mM Na$_2$HPO$_4$, 1.5 mM KH$_2$PO$_4$) or 100 ul of purified rabbit IgG F(ab')2. The plates were washed three times with wash-buffer (0.5% Tween 20 in PBS) and blocked for 2 hours in Blotto (5% nonfat dry milk in PBS). After three washes with wash-buffer, *B. burgdorferi*-free culture supernatants from B31V and B31A were added to the plates for 2 hours at room temperature. Culture supernatants were evaluated against a reference curve obtained by serial dilutions of known amounts of rEppA in medium identical to the culture supernatants. Plates were washed three times with wash-buffer and incubated with 100 ul of rabbit anti-EppA serum (1:2000 dilution in Blotto) for 2 hours at room temperature. Following three washes with wash-buffer, the plates were incubated for 2 hours at room temperature with 100 ul of Protein A-HRP conjugate (1:2000 dilution in Blotto) (Amersham). The plates were then washed and 100 ul of ABTS peroxidase substrate system (Kirkgaard & Perry, Gaithersburg, Md.) was added to each well for color development. After 30 minutes, the reaction was stopped by the addition of 100 ul of 1% SDS, and the $OD_{405}$ of each well was measured on an automated ELISA plate reader (Titertek Multiskan MCC/340, Flow Laboratories, Baar, Switzerland).

Localization of EppA in *E. coli*

A 522-bp BamHI-EcoRI fragment containing the eppA gene including the sequence encoding the signal peptide was generated by PCR utilizing primers CC03 and CC04 (Table 2) and ligated into the expression vector pMMB66HE (Furste, et al., *Gene*, 48:119–131, 1986) digested with BamHI and EcoRI. The resultant plasmid, pMMB66HE-eppA was transformed into DH5α. DH5α harboring pMMB66HE-eppA was grown to an $OD_{600}$ of 0.3 and induced for 1 hour with 100 uM IPTG. The cells were centrifuged at 10,000×g for 10 minutes and resuspended to a final concentration of $2\times10^{10}$/ml in 50 mM Tris-HCl (pH 8.0)-5 mM EDTA followed by the addition of lysozyme to a final concentration of 100 ug/ml. The culture supernatant was evaluated for the presence of secreted EppA by the antigen-capture ELISA described above. Following resuspension, the cells were disrupted by sonication and the soluble (cytoplasm and periplasm), cytoplasmic membrane, and outer membrane fractions were separated by sucrose density gradient centrifugation as described by Thom and Randall (Thom, et al., *J. Bacterial*, 170:5654–5661, 1988). After centrifugation, 1 ml fractions were collected from the top of the gradient and 10% of each fraction was used to determine β-NADH oxidase activity (Osborn, et al., *J. Biol. Chem.*, 247:3962–3972, 1972). In addition, 10% of the total lysate before separation as well as each fraction were analyzed by SDS-PAGE and immunoblotting as described above. Membranes were probed with a 1:10,000 dilution of rabbit anti-OmpA antiserum and a 1:1000 dilution of rabbit anti-EppA antiserum.

Alkali and salt treatment of the outer membrane fraction of *E. coli* containing rEppA The enriched outer and cytoplasmic membrane fractions were concentrated by centrifugation at 141,000×g for 2 hours and resuspended in 50 μl PBS. Eight microliters of membrane sample was added to 50 μl of either 0.1M $Na_2CO_3$ (pH 11.5), 1M NaCl, or 0.1N NaOH (pH 11.0), and incubated for 1 min at room temperature followed by the addition of 850 μl of 50 mM $Na_2HPO_4$ (pH 6.8) in order to neutralize the sample. Samples were then centrifuged at 41,000×g for 1 hour and then the membrane pellets were resuspended in 20 μl of 2× FSB. The supernatants containing released proteins were TCA precipitated and resuspended 20 μl 2× FSB. All samples were analyzed by SDS-PAGE and immunoblotting as described above.

Nucleotide sequence accession number

The DNA sequence reported here has been deposited in GenBank with the accession number L16625.

Example 2

Clonong of the eppA Gene

To isolate the eppA gene, an oligonucleotide was generated based on the previously determined nucleotide sequence of the amino terminus of Bb244 (Giladi, et al., supra). The probe, CC01 (SEQ ID NO:3), hybridized to a 3.3 kbp EcoRV-HincII fragment by Southern blot analysis of the 9.0-kbp circular plasmid (Table 2). A λZAP II library of the 9.0-kbp circular plasmid was generated with EcoRI-adapted EcoRV-HincII restriction fragments of this plasmid and probed with CC01 (see Example 1). Four positive plaques were isolated, replated twice, and reprobed each time with CC01. The four phage clones were amplified and converted to the pBluescript SK(-) plasmid by in vivo excision. All four clones contained the same 3.3-kbp EcoRI insert. One clone designated pBb1, was chosen for further analysis. A partial restriction map of pBb1 was constructed, and Southern hybridization with CC01 localized the region of hybridization to a 115-bp StyI-HindIII fragment.

FIG. 1 shows a partial restriction map of the 3.3-kbp EcoRI fragment in pBb1. The shaded area in indicates the location of the EppA signal peptide. The open boxed area indicates the coding region for mature EppA. (bp, Base pairs).

1. DNA Sequence of eppA

An open reading frame was identified approximately 2.1-kbp downstream from the EcoRI site. The nucleotide and the deduced amino acid sequence are shown in FIG. 2 and SEQ ID NO:1 and SEQ ID NO:2. The eppA gene consists of an open reading frame of 522-bp encoding a precursor protein of 174 amino acids (20,277 Da) with typical N-terminus characteristics of a signal peptide; an amino terminus beginning with methionine and basic charged residues, a hydrophobic core, and a leader peptidase I recognition site containing the amino acid sequence, Leu-Ser-Ala. A mature protein of 154 amino acids (17,972 Da) is predicted following cleavage with leader peptidase I. A putative Shine-Dalgarno ribosome binding site was identified along with a -10 and -35 promoter-like region which is similar to other previously reported Borrelia genes (Bergstrom, et al., supra; Fuchs, et al., supra; Lam, et al., supra; Marconi, et al., *J. Bacteriol.*, 175:926–932, 1993; Norris, et al., supra). In addition, dyad symmetrical sequences were identified within the -35 region suggesting that eppA is transcriptionally regulated (Silver, et al., *Microbiol. Rev.*, 56:195–228, 1992). The putative ribosome-binding site (RBS) and -10 and -35 promoter regions are underlined. A region of dyad symmetry within the -35 promoter site is indicated by inverted arrows. The leader peptidase I cleavage site is noted by an arrow (↑). The location of the TAA stop codon is indicated by an asterisk. Sequence location for PCR primers CC01, CC02 (SEQ ID NO:4), and CC03 (SEQ ID NO:5) are indicated. A search of the GenBank data base did not reveal amino acid sequence homologies.

2. Northern Blot Analysis

Figure 3:
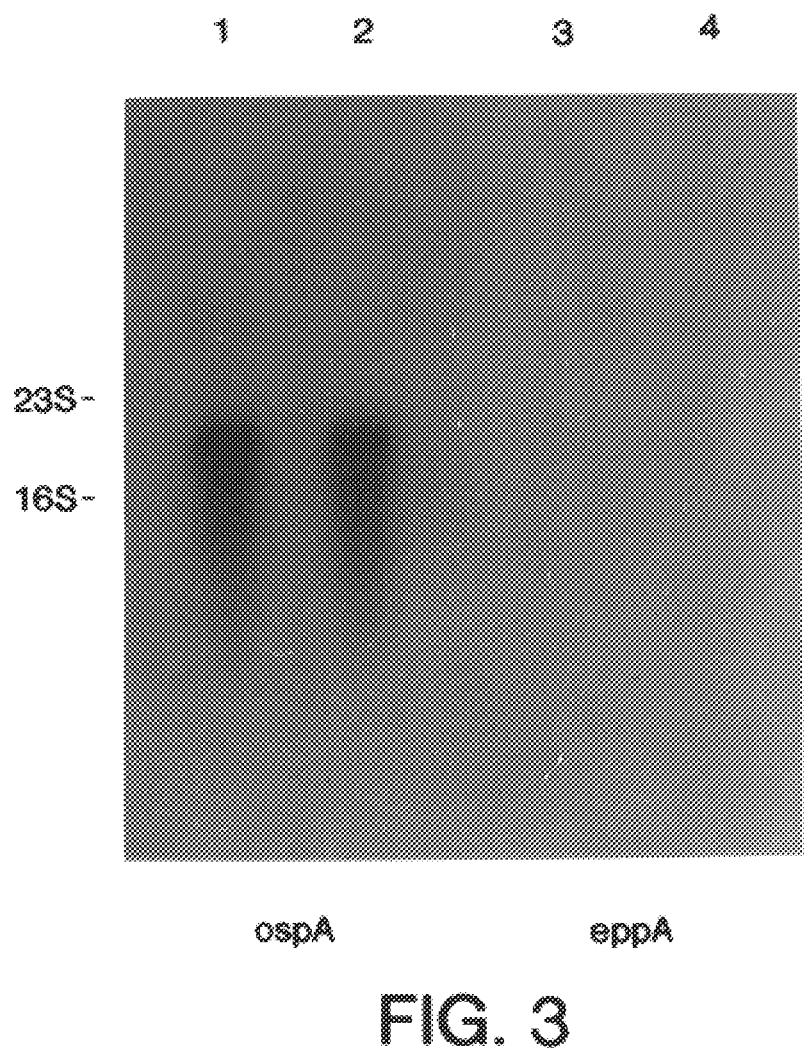
FIG. 3 shows the Northern blot analysis of eppA transcription. Fifteen micrograms of total cellular RNA isolated from B31V (lanes 1 and 3) and B31A (lanes 2 and 4) were separated by electrophoresis and transferred to nitrocellulose. The membrane was hybridized with radiolabled DNA probes specific for ospA (lanes 1 and 2) and for eppA (lanes 2 and 4). The positions of 23S and 16S rRNAs are indicated.

Total cellular RNA from B31V (passage 2) and B31A was analyzed by Northern hybridization. FIG. 3 shows the Northern blot analysis of eppA transcription. Fifteen micrograms of total cellular RNA isolated from B31V (lanes 1 and 3) and B31A (lanes 2 and 4) were separated by electrophoresis and transferred to nitrocellulose. The membrane was hybridized with radiolabled DNA probes specific for ospA (lanes 1 and 2) and for eppA (lanes 2 and 4). The positions of 23S and 16S rRNAs are indicated.

Hybridization with a 522-bp PCR product generated with primers CC02 and CC03 failed to detect an eppA transcript (FIG. 3, lanes 3 and 4). As a control for in vitro expression and RNA degradation, the same RNA was probed with a PCR product generated by primers ospA-1 and ospA-2. The previously reported 2.2-kb ospAB transcript was identified indicating the intact Borrelia transcripts were present in the RNA preparation (FIG. 3, lanes 1 and 2). These results suggest either that (i) eppA is not transcribed during in vitro cultivation, (ii) the transcript is generated but quickly degraded, or (iii) the transcript is at very low levels not detectable by this technique.

Example 3

Expression and Purification of rEppA.

Figure 4:
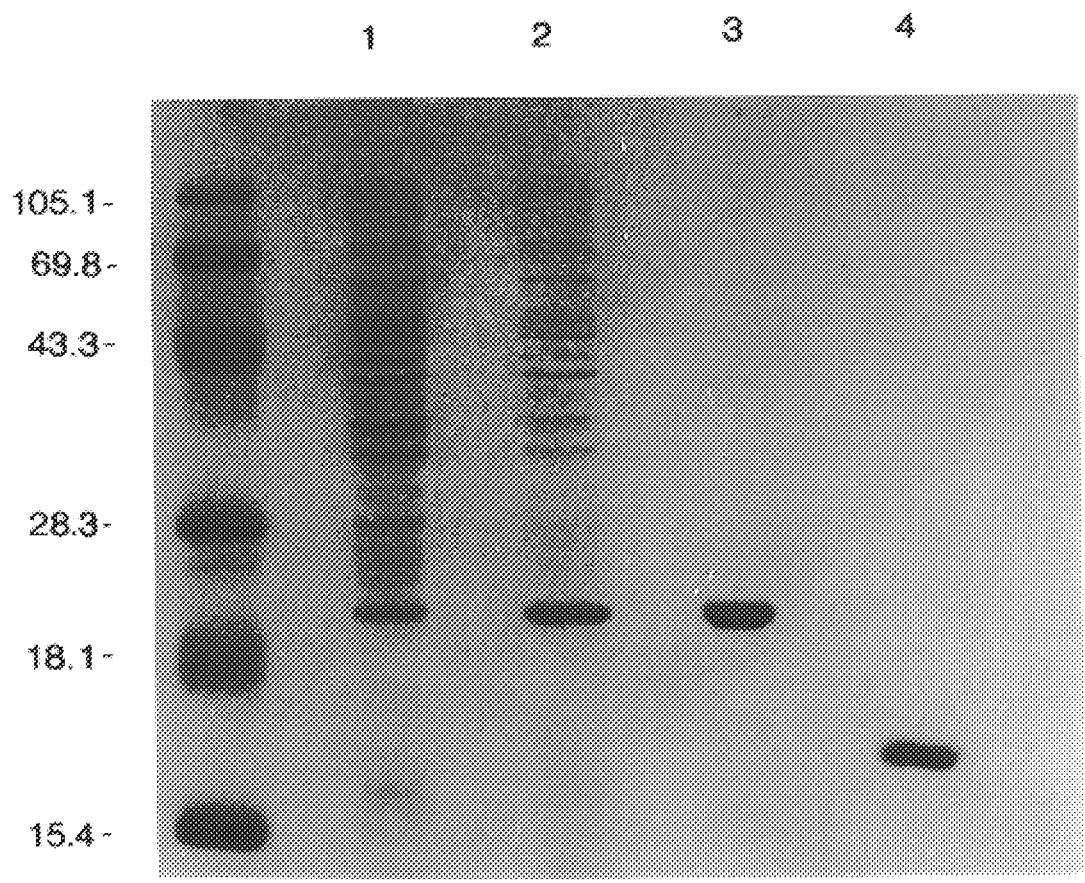
FIG. 4 shows the expression and purificaiton of rEppA. Total protein from uninduced cells (lane 1), cells induced with 1 mM IPTG for 4 hours in the presence of rifampicin (200 $\mu$g/ml) (lane 2), purified $His_6$-EppA fusion protein (lane 3), and enterokinase-cleaved purified rEppA (lane 4) were separated by SDS-PAGE (12.5%) and visualized by Coomassie blue staining. Samples in lanes 1 and 2 were equivalent to 150 $\mu$l of culture and samples in lanes 3 and 4 contain approximately 10 $\mu$g. Molecular masses (in kilodaltons) of prestained protein markers are indicated.

Expression and purification of rEppA in *E. coli* strain JM109 (DE3) is shown in FIG. 4. Total protein from uninduced cells (lane 1), cells induced with 1 mM IPTG for 4 hours in the presence of rifampicin (200 µg/ml) (lane 2), purified $His_6$-EppA fusion protein (lane 3), and enterokinase-cleaved purified rEppA (lane 4) were separated by SDS-PAGE (12.5%) and visualized by Coomassie blue staining. Samples in lanes 1 and 2 were equivalent to 150 µl of culture and samples in lanes 3 and 4 contain approximately 10 µg. Molecular masses (in kilodaltons) of prestained protein markers are indicated.

The pRSET-eppA construct expressed a fusion protein approximately 22,000 molecular weight (lane 3) where the T7 gene 10 fusion peptide contributes an additional 3,800 daltons. Enterokinase cleavage of this fusion yielded a protein of approximately 17,000 molecular weight (lane 4), consistent with the size EppA predicted from the deduced amino acid sequence.

Example 4

Absence of EppA in In Vitro Cultiveted *B. burgdoferi*

Figure 5:
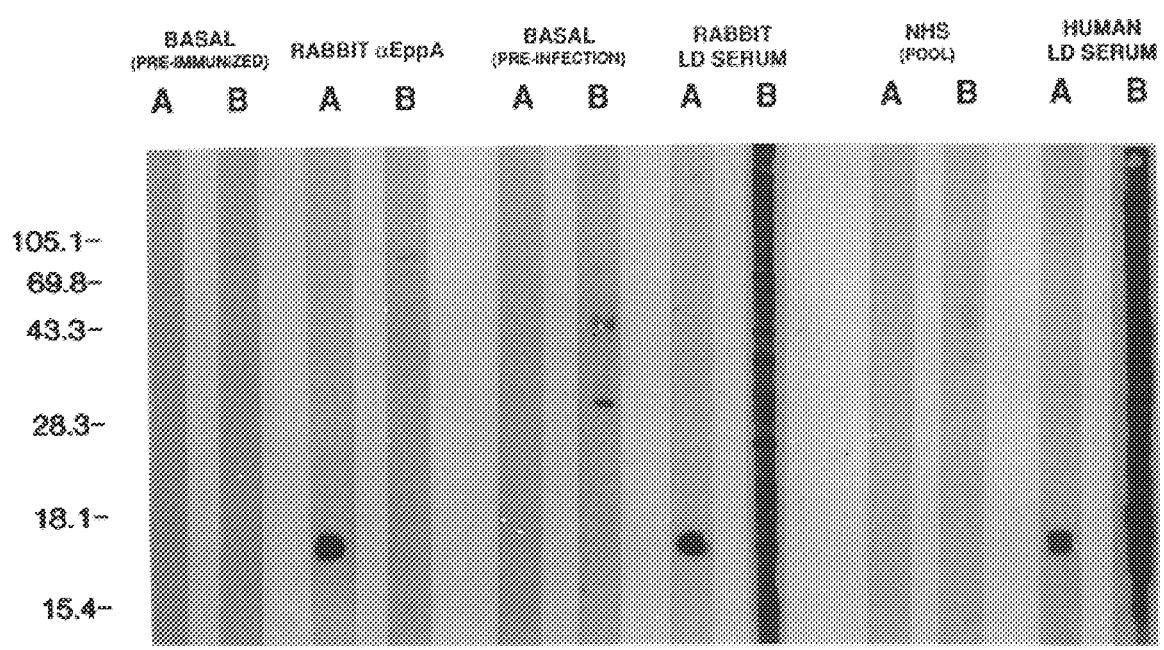
FIG. 5 shows the absence of EppA from in vitro cultivated *B. burgdorferi* and detection of anti-EppA antibodies in Lyme disease (LD) sera. Antigen strips containing 10 $\mu$g of rEppA (A) and $1\times10^9$ B31V (B) were reacted against serum obtained from rabbits immunized with rEppA (Rabbit $\alpha$-EppA) at a 1:1000 dilution, serum obtained from a rabbit infected for 6 months with B31V (Rabbit LD serum) at a 1:100 dilution, and serum obtain from a Lyme disease patient (Human LD serum) at a 1:250 dilution. Control strips containing 10 $\mu$g of rEppA (A) and $1\times10^9$ B31V (B) were reacted against a serum pool of rabbits prior to immunization with rEppA (Basal pool/preimmunization) at a dilution of 1:1000, with pre-infection serum (Basal/pre-infection) at a 1:100 dilution, and with a pool of normal human serum (NHS Pool) at a 1:250 dilution. Molecular masses (in kilodaltons) of prestained protein markers are indicated.

Anti-EppA serum generated in rabbits (EXAMPLE 1) was used in immunoblot analysis to identify recombinant and native EppA. The level of sensitivity of this antiserum at the dilution used was capable of detecting as little as 5 ng of rEppA. FIG. 5 shows the absence of EppA from in vitro cultivated *B. burgdorferi* and detection of anti-EppA antibodies in Lyme disease (LD) sera. Antigen strips containing 10 µg of rEppA (A) and $1 \times 10^9$ B31V (B) were reacted against serum obtained from rabbits immunized with rEppA (Rabbit α-EppA) at a 1:1000 dilution, serum obtained from a rabbit infected for 6 months with B31V (Rabbit LD serum) at a 1:100 dilution, and serum obtain from a Lyme disease patient (Human LD serum) at a 1:250 dilution. Control strips containing 10 µg of rEppA (A) and $1 \times 10^9$ B31V (B) were reacted against a serum pool of rabbits prior to immunization with rEppA (Basal pool/preimmunization) at a dilution of 1:1000, with pre-infection serum (Basal/pre-infection) at a 1:100 dilution, and with a pool of normal human serum (NHS Pool) at a 1:250 dilution. Molecular masses (in kilodaltons) of prestained protein markers are indicated.

As shown in FIG. 5, anti-EppA antibodies were unable to detect EppA from $1 \times 10^9$ in vitro cultivated B31V (passage 2). In contrast, a representative serum sample from both a human Lyme disease patient as well as from an experimentally infected rabbit which exhibited erythema migrans-like lesions contained antibodies that recognized rEppA. Rabbit sera from pre-immunized and pre-infection as well as sera from normal humans did not react with rEppA.

To determine whether EppA is secreted into the medium by *B. burgdorferi*, an antigen-capture ELISA was performed using purified rabbit anti-EppA IgG F(ab')2 fragments and rabbit IgG F(ab')2 fragments as a control. The level of sensitivity of this assay for EppA was determined to be 0.4 ng/ml (40 pg/well) based on a standard reference curve using rEppA added to BSK II media. The culture supernatants from both B31V (passage 2) and B31A had no detectable levels of EppA. The inability to detect EppA in a B31V protein lysate or in the supernatant of in vitro grown B31V via ELISA is consistent with the Northern blot finding and demonstrates that eppA expression during in vitro cultivation, if any, is below the level of detection utilizing these methods.

Example 5

Localization of rEppA Expressed in *E. coli*

Figure 6A:
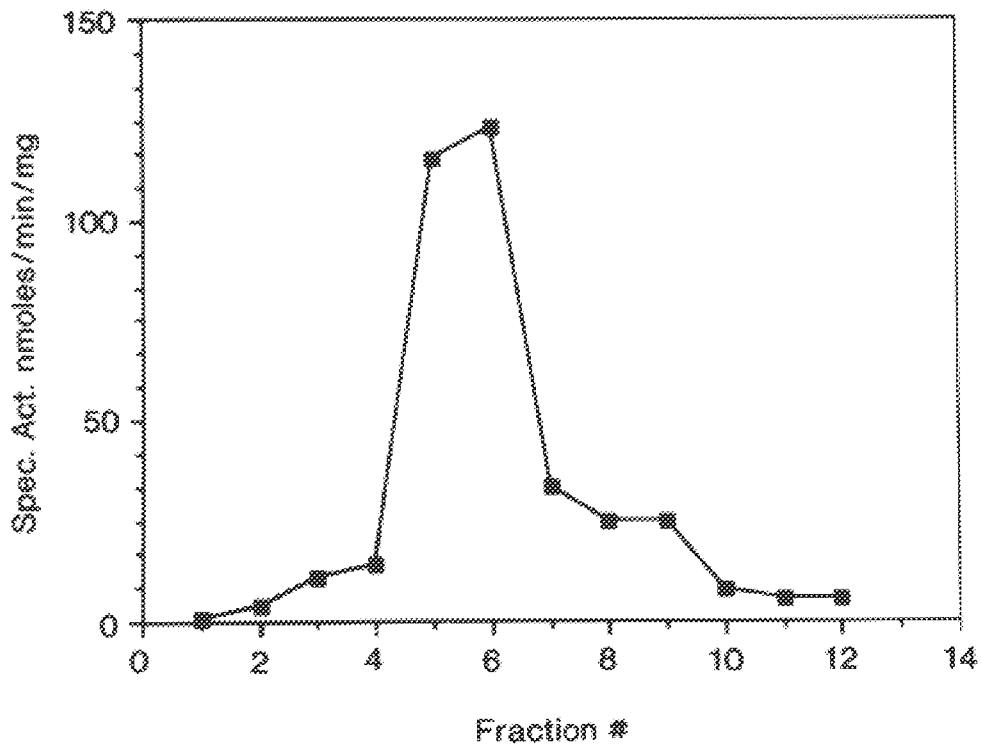
FIGS. 6A–6D show studies to determine the localization of rEppA in *E. coli* DH5$\alpha$ containing pMMB66HE-eppA.
Figure 6B:
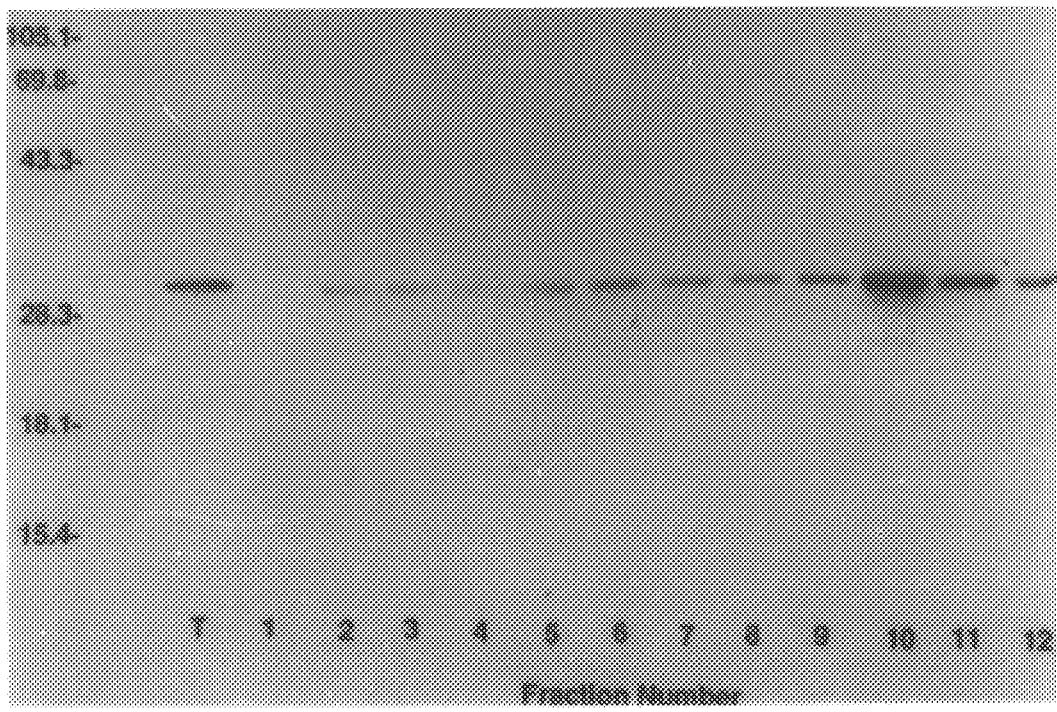
Figure 6C:
Figure 6D:
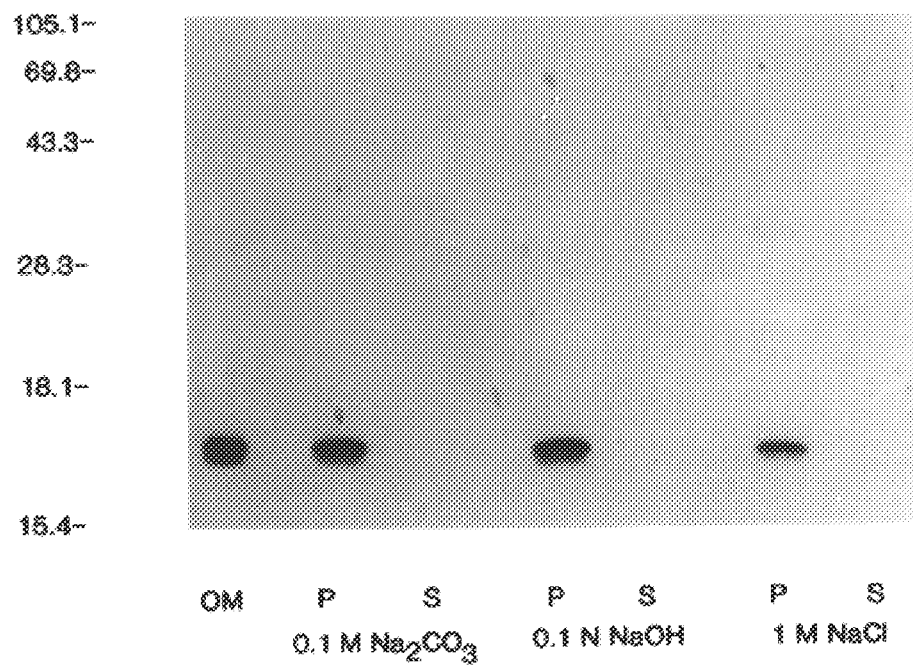

Because too few spirochetes are found in vertebrate infection to allow studies aimed at cellular location of EppA, the fate of rEppA when expressed in *E. coli* was examined. To determine the localization of rEppA in *E. coli*, a exponentially growing culture of *E. coli* DH5α containing pMMB66HE-eppA was induced for 1 hour with 100 µM IPTG (FIGS. 6A–6D). Preparation of the cellular lysate and fractionation over a sucrose density gradient were performed as described in Example 1. FIG. 6A shows the separation of cytoplasmic membrane from outer membrane (OM) based on β-NADH oxidase activity (■). FIGS. 6B and 6C are identical immunoblots containing 10% of each fraction (1–12, T=total lysate before gradient) incubated with 1:10,000 dilution of rabbit anti-OmpA and 1:1000 dilution of rabbit anti-EppA, respectively. FIG. 6D is a immunoblot of alkali and high salt treatment of the enriched OM fraction. The OM was treated with 0.1M $Na_2CO_3$ (pH 11.5) (lanes 2 and 3), 0.1N NaOH (pH 11.0) (lanes 4 and 5), and 1M NaCl (lanes 6 and 7), followed by centrifugation to separate soluble (S) from the membrane pelleted (P) material. The samples were separated on a SDS-12.5% polyacrylamide gel, transferred to Immobilon-P, and incubated with a 1:1000 dilution of rabbit anti-EppA. Molecular masses (in kilodaltons) of prestained protein markers are indicated.

The cytoplasmic and outer membrane fractions were identified based on SDS-PAGE compositional analysis, immunoblot analysis using anti-OmpA antisera to identify the outer membrane fractions (FIG. 6B), and by the distribution of β-NADH oxidase activity which serves as a marker for the cytoplasmic membrane (FIG. 6A). Based on the results of the β-NADH oxidase assay, fractions 5 and 6 contained the majority of the cytoplasmic membrane. Anti-OmpA (FIG. 6B) indicated that fraction 10 was enriched for the outer membrane although some OmpA was present in the other fractions except fraction 1 which contained the majority of the soluble proteins. Immunoblot analysis of the same filter reprobed with rabbit anti-EppA showed that approximately equal amounts of rEppA was detected in both cytoplasmic and outer membrane fractions (FIG. 6C). To determine if rEppA was either integrated or peripherally associated with the outer membrane, the outer membrane fraction was exposed to alkali and high salt treatments which releases non-integral membrane proteins while leaving the membrane lipid bilayer structure intact. As shown in FIG. 6D, rEppA remained membrane anchored despite treatment with 0.1M $Na_2CO_3$ (pH 11.5), 0.1N NaOH (pH 11.0), and 1M NaCl. Identical results were obtained from the cytoplasmic membrane fraction. In addition, the culture supernatant from *E. coli* harboring pMMB66HE-eppA had no detectable levels of secreted rEppA as determined by the antigen-capture ELISA described above. These findings indicated that rEppA expressed in E. coli becomes integrally membrane associated.

TABLE 1

BACTERIAL STRAINS AND PLASMIDS

| Strain or plasmid | Description |
|---|---|
| E. coli[a] | |
| DH5α | F-hsdR17 supE44 thi-1 recA1 Δ(argF-lac) U169 φ80dlacZΔM15 λ-endA1 |
| | recA1 gyrA96 thi hsdR17 (r-k,m + k) relA1 supE44 Δ(lac-proAB) [F traD36 |
| JM109(DE3) | proAB laclqZΔM15]λ(DE3) |
| B. Burgdorferi | |
| B31V[b] | A virulent isolate from the spleen of a C3H mouse passed two times in vitro. |
| B31A[c] | A multi-passaged (>200), avirulent strain of B31 which lacks the 9.0-kbp circular plasmid |
| Plasmids | |
| pBb1 | original pBluescript SK-isolate rescued from the λZAP II library of the 9.0-kbp supercoiled plasmid with a 3.3-kbp EcoRI fragment containing eppA. |
| pRSET[d] | E. coli fusion expression vector encoding 35 amino acids of the T7 gene 10 fused to an enterokinase recognition site adjacent to 6 histidine residues enabling purification of fusion protein over a Nickel column. Contains the T7 promoter and transcription terminator. |
| pRSET-eppA | 477-bp eppA gene fragment lacking the signal sequence derived from PCR primers CC02/CC03 ligated into pRSET cleaved with BamHI-EcoRi |
| pMMB66HE[e] | E. coli low copy number expression vector containing the tac promoter |
| pMMB66HE-eppA | 522-bp eppA gene fragment containing the signal sequence derived from PCR primers CC03/CC04 ligated into pMMB66HE cleaved with BamHI-EcoRi |

[a]Promega
[b]S. Barthold, et al., J. Infect. dis., 157:842-846, 1988
[c]ATCC 35210
[d]Invitrogen
[e]Furste, et al., Gene, 48:119-131, 1986 levels by the ability to bind to EppA antigen in an ELISA. Briefly, flat-bottom, 96-well lmmunlon microtiter plates were coated with purified rEppA (50 ng/well) in PBS (0.5 ug/ml) at room temperature overnight in a humidified chamber, and washed with PBS-T wash buffer (0.14M NaCl, 2.7 mM KCl, 4.3 mM $Na_2 HPO_4$, 1.5 mM $KH_2 PO_4$; 0.5 ml Tween-20 per 1 liter of 1×PBS) then incubated with 250 μl of 5% Blotto blocking buffer (5% nonfat dry milk in PBS) for one hour at room temperature in a humidified chamber and washed 2× prior to analysis with PBS-T wash buffer. Sera, diluted 1:100 in blocking buffer (100 μl/well), was added to each well in duplicate, and the plates were incubated for 2 hours at room temperature. The plates were then washed with PBS-T wash buffer 3–4 times and 1:5000 sheep anti-human Ig-HRP (for human samples) (Amersham, 100 μl/well) or 1:5000 donkey anti-rabbit Ig-HRP conjugate was added to the washed plates, diluted 1:5000 in blocking buffer and incubated for 1 hour at room temperature in a humidified chamber. The plates were washed 3–4 times with PBS-T and 100 μl of ABTS peroxidase substrate system (Kirkegaard & Perry) (ABTS Peroxidase Substrate System—mix equal volumes of ABTS peroxidase substrate with peroxidase solution B) was added to each well and incubated for 30 minutes in the dark at room temperature in a humidified chamber and stopped with the addition of 100 μl per well of 1% SDS. The substrate hydrolysis color development was measured at 405 nm on an automated ELISA microtiter plate reader (Titertek Multiskan MCC/340, Flow Laboratories).

The results are shown in Tables 3 and 4. Table 3 shows the $OD_{405}$ for 77 samples of normal human serum. The mean OD405 was 0.082 (SD=0.036). Any value greater than or equal to 0.154 was considered to be reactive. Only 6/77 serum samples were considered reactive. The specificity of this test was 92.2%. In contrast, Table 4 shows the results for 63 serum samples from patients diagnosed with Lyme disease. The patients had various clinical symptoms such as arthritis, neurologic symptoms, anthralgia and erythema migrans. The results show that 85% of the 63 patients with documented Lyme borreliosis had antibodies which bind

TABLE 2

OLIGONUCLEOTIDES

| Designation | Sequence | Description or Purpose |
|---|---|---|
| CC01 | 5'-ATGAGAAAAATAAGCCTA-3'<br>SEQ ID NO:3 | Nucleotides 159–176 used for Southern and plaque hybridizations |
| CC02 | 5'-CGCGGATCCTTTATGAGTCAAGATATAAAA-3'<br>SEQ ID NO:4 | Nucleotides 219–239 used for PCR (incorporated BamHI site underlined) |
| CC03 | 5'-CCGGAATTCTTAATCTTTAGGCAAGTCTGCC-3'<br>SEQ ID NO:5 | Nucleotides 683–662 used for PCR (made to 3' strand, incorporated EcoRI site underlined) |
| CC04 | 5'-CGCGGATCCATGAGAAAAATAAGCCTA-3'<br>SEQ ID NO:6 | Nucleotides 159–176 used for PCR (same as CC01 except a BamHI has been incorporated) |
| OspA-1 | 5'-ATGAAAAAATATTTATTGGGA-3'<br>SEQ ID NO:7 | PCR primer made to beginning of ospA |
| OspA-2 | 5'-TTTTAAAGCGTTTTTAATTTCA-3'<br>SEQ ID NO:8 | PCR primer made to end of ospA from the 3' strand |

Example 6
Comparison of Levels of EppA Antibody in Normal Vs. Lyme Disease Sera

Serum from humans diagnosed with Lyme disease and normal human serum were assessed for EppA antibody purified rEppA as determined by ELISA. Therefore, a great majority of humans infected with B. burgdorferi make EppA specific antibodies, suggesting that EppA correlates with infectivity for humans.

TABLE 3

EppA ANTIGEN EVALUATION IN NORMAL HUMAN SERA

| Sera No. | Mean/SD | Sera No. | Mean/SD |
|---|---|---|---|
| 1 | 0.084/0.002 | 26 | 0.236/0.21* |
| 2 | 0.059/0.002 | 27 | 0.108/0.004 |
| 3 | 0.123/0.002 | 28 | 0.082/0.007 |
| 4 | 0.087/0.008 | 29 | 0.141/0.009 |
| 5 | 0.090/0.006 | 30 | 0.080/0.006 |
| 6 | 0.045/0.003 | 31 | 0.145/0.008 |
| 7 | 0.057/0.008 | 32 | 0.099/0.003 |
| 8 | 0.074/0.002 | 33 | 0.075/0.003 |
| 9 | 0.084/0.005 | 34 | 0.075/0.008 |
| 10 | 0.156/0.026* | 35 | 0.075/0.001 |
| 11 | 0.057/0.001 | 36 | 0.273/0.004* |
| 12 | 0.092/0.009 | 37 | 0.058/0.005 |
| 13 | 0.097/0.013 | 38 | 0.125/0.009 |
| 14 | 0.077/0.006 | 39 | 0.103/0.001 |
| 15 | 0.072/0.006 | 40 | 0.053/0.003 |
| 16 | 0.056/0.006 | 41 | 0.047/0.002 |
| 17 | 0.049/0.003 | 42 | 0.068/0.001 |
| 18 | 0.056/0.002 | 43 | 0.086/0.005 |
| 19 | 0.111/0.002 | 44 | 0.082/0.000 |
| 20 | 0.088/0.003 | 45 | 0.025/0.003 |
| 21 | 0.043/0.004 | 46 | 0.135/0.009 |
| 22 | 0.050/0.002 | 47 | 0.076/0.004 |
| 23 | 0.053/0.003 | 48 | 0.051/0.004 |
| 24 | 0.094/0.002 | 49 | 0.094/0.004 |
| 25 | 0.063/0.001 | 50 | 0.046/0.005 |
| 51 | 0.060/0.002 | 65 | 0.127/0.022 |
| 52 | 0.085/0.001 | 66 | 0.141/0.004 |
| 53 | 0.057/0.005 | 67 | 0.092/0.002 |
| 54 | 0.078/0.016 | 68 | 0.072/0.003 |
| 55 | 0.075/0.008 | 69 | 0.091/0.006 |
| 56 | 0.041/0.002 | 70 | 0.054/0.002 |
| 57 | 0.041/0.002 | 71 | 0.205/0.0115* |
| 58 | 0.076/0.003 | 72 | 0.123/0.003 |
| 59 | 0.087/0.003 | 73 | 0.099/0.005 |
| 60 | 0.069/0.002 | 74 | 0.098/0.016 |
| 61 | 0.118/0.003 | 75 | 0.229/0.002* |
| 62 | 0.096/0.001 | 76 | 0.101/0.004 |
| 63 | 0.163/0.023* | 77 | 0.066/0.003 |

The mean $OD_{405}$ for 77 NHS is 0.082
The SD is 0.036
The cutoff value is the mean + 2SD = 0.154
Any values greater than or equal to .154 is considered reactive
*indicate normals above the cutoff value (6)
Specificity = $\frac{77-6}{77} \times 100 = 92.2\%$

TABLE 4

EppA ANTIGEN EVALUATION IN LYME PATENT SERA

| Sera No. | Clinical Observations | Mean/SD |
|---|---|---|
| 1 | Heart block several weeks after tick bite | 1.965/0.100 |
| 2 | Arthritis | 0.923/0.127 |
| 3 | Anthralgia | 0.148/0.001* |
| 4 | Anthralgia | 3.000/0.000 |
| 5 | Neurologic | 0.115/0.009* |
| 6 | Arthritis | 1.024/0.025 |
| 7 | Arthritis | 2.855/0.206 |
| 8 | Arthritis | 1.023/0.112 |
| 9 | Arthritis | 0.111/0.002* |
| 10 | Arthritis | 1.812/0.084 |
| 11 | Bell's palsy | 1.719/0.015 |
| 12 | Persistent anthralgia | 1.021/0.021 |
| 13 | Anthralgia | 0.226/0.011 |
| 14 | Arthritis | 3.000/0.000 |
| 15 | Anthralgia | 1.099/0.049 |
| 16 | Anthralgia | 0.294/0.014 |
| 17 | Arthritis | 0.212/0.001 |
| 18 | Arthritis & Neurologic | 2.436/0.007 |
| 19 | Arthritis | 3.000/0.000 |
| 20 | Arthritis | 0.233/0.008 |
| 21 | Arthritis | 1.220/0.402 |
| 22 | Arthritis | 2.496/0.310 |
| 23 | Arthritis | 0.239/0.002 |
| 24 | Arthritis | 2.908/0.131 |
| 25 | joint pain | 0.416/0.001 |
| 26 | joint pain | 0.613/0.100 |
| 27 | Arthritis | 1.076/0.005 |
| 28 | Arthritis | 2.459/0.025 |
| 29 | Arthritis | 1.400/0.220 |
| 30 | Arthritis | 0.169/0.013 |
| 31 | Neurologic | 2.755/0.033 |
| 32 | Neurologic | 0.255/0.000 |
| 33 | Neurologic | 0.337/0.010 |
| 34 | Neurologic | 0.208/0.010 |
| 35 | Neurologic | 0.376/0.028 |
| 36 | Neurologic | 0.321/0.031 |
| 37 | Neurologic | 0.898/0.417 |
| 38 | Neurologic | 0.111/0.036* |
| 39 | Neurological | 0.090/0.007* |
| 40 | Anthralgia | 0.120/0.000* |
| 41 | Unknown | 2.757/0.110 |
| 42 | Unknown | 0.435/0.030 |
| 43 | Arthritis | 0.305/0.011 |
| 44 | Unknown | 1.761/0.000 |
| 45 | Neurologic | 0.239/0.006 |
| 46 | Neurologic | 0.261/0.029 |
| 47 | Asymptomatic seroconverter | 0.256/0.025 |
| 48 | Erythema migrans | 0.134/0.029* |
| 49 | Arthritis | 1.535/0.001 |
| 50 | Arthritis & Neurologic | 0.517/0.038 |
| 51 | Neurologic | 1.390/0.013 |
| 52 | Neurologic | 0.260/0.017 |
| 53 | Arthritis | 0.364/0.017 |
| 54 | Erythema migrans | 0.091/0.004* |
| 55 | Neurologic | 2.090/0.055 |
| 56 | Erythema migrans | 0.192/0.001 |
| 57 | Erythema migrans | 0.234/0.005 |
| 58 | Erythema migrans | 0.356/0.076 |
| 59 | Erythema migrans | 0.167/0.022 |
| 60 | Erythema migrans | 0.119/0.009* |
| 61 | Erythema migrans | 0.191/0.009 |
| 62 | Arthritis | 0.664/0.062 |
| 63 | Arthritis | 0.134/0.020* |

As determined from the 77 normals the cutoff value for reactivity is 0.154. Therefore, *indicates those sera non-reactive to EppA.
Sensitivity = $\frac{63-10}{63} \times 100 = 84.1\%$

Example 7

Location of EppA in the Outer Membrane

Because the predicted amino acid sequence of EppA indicates the presence of a signal peptide cleaved by leader peptidase I and because previous studies have shown that EppA-PhoA fusions are exported across the cytoplasmic membrane (Giladi, et al., *J. of Bacteriol.*, 175:4129–4136, 1993), it is likely that EppA is either directed to the periplasm, outer membrane, or is secreted. Since eppA expression is not detectable during in vitro cultivation of *B. burgdorferi* and the paucity of spirochetes in vertebrate infection precludes studies aimed at determining the native cellular location of this protein, information regarding its possible cellular location was examined in *E. coli*. These findings indicated that rEppA when expressed in *E. coli* becomes integrated in the outer membrane (see Example 5).

Based on these findings, an experiment was performed to determine whether rEppA had the capability of incorporating into proteolipsomes. Purified rEppA in 10 mM Tris/0.2 mM EDTA, pH 8.0, 1.25% octylglucoside, and 8M Urea was mixed with *E. coli* phospholipids (Avanti Polar Lipids) at a 100:1 phospholipid to protein molar ratio. In addition, liposomal vesicles were made without rEppA, as a control. The samples were dialyzed against 10 mM Tris/0.2 mM EDTA, pH 8.0 at room temperature with buffer exchanges every 12 hours for a total of 48 hours. The membrane vesicles from both samples were pelleted at 235,000×g for 2 hours at 8° C. and washed once under the same conditions. Following the wash, the membrane pellets were resuspended in PBS and processed for lmmunoelectronmicroscopy (IEM). Briefly, 5 ul of each sample was adsorbed to EM grids for 5 minutes at room temperature. The grids were blocked with 50% normal goat serum in EM Blocking buffer (0.3M NaCl, 0.05M HEPES, pH 7.5, 0.1% NaN$_3$, 0.1% Teleostean fish gelatin, 1% BSA) for 30 minutes in a moist chamber at room temperature. The grids were then incubated on 20 ul drops of rabbit anti-EppA antiserum or normal rabbit serum (control) at a 1:50 dilution for 1 hour at room temperature. Following incubation, the grids were washed 8 times with EM Wash buffer (0.9% NaCl, 0.05M HEPES, pH 7.5, 0.1% NaN$_3$); 2–3 minutes/wash. The grids were then incubated on 20 ul drops of a 1:30 Protein A-gold labeled (10 nm in size) (Sigma) for 1 hour at room temperature. The grids were washed again as described above and subsequently stained with 1% Uranyl acetate for 40 seconds and examined under the electron microscope.

The results, based on gold particles found on the membrane vesicles containing rEppA, indicated that rEppA protein specifically associates under these conditions with the artificially created liposomal membrane vesicles. These results further suggest that EppA may be a transmembrane protein and therefore an outer membrane protein of *B. burgdorferi*. The control with normal rabbit serum reacted against the rEppA proteoliposome vesicles did not show any substantial amount of gold particles.

The foregoing is meant to illustrate, but not to limit, the scope of the invention. Indeed, those of ordinary skill in the art can readily envision and produce further embodiments, based on the teachings herein, without undue experimentation.

SUMMARY OF SEQUENCES

SEQ ID NO:1 is the nucleotide and deduced amino acid sequence of eppA.

SEQ ID NO:2 is the deduced amino acid sequence of EppA.

SEQ ID NO:3 is the nucleotide sequence of primer CC01, or nucleotides 159–176 of eppA.

SEQ ID NO:4 is the nucleotide sequence of primer CC02, or nucleotides 219–239 of eppA.

SEQ ID NO:5 is the nucleotide sequence of primer CC03, or nucleotides 683–662 of eppA.

SEQ ID NO:6 is the nucleotide sequence of primer CC04, or nucleotides 159–176 (plus a BamHI site) of eppA.

SEQ ID NO:7 is the nucleotide sequence of a primer to the beginning of ospA.

SEQ ID NO:8 is the nucleotide sequence of a primer to the end of ospA from the 3' strand.

---

We claim:
1. An isolated EppA (exported plasmid protein A) polypeptide, wherein the polypeptide has an amino acid sequence of SEQ ID NO:2.

* * * * *